United States Patent [19]

Curtis

[11] E Patent Number: Re. 33,409

[45] Reissued Date of Patent: Oct. 30, 1990

[54] GRIP ASSEMBLY

[76] Inventor: John M. Curtis, R.D. 5, Box 375, Kittanning, Pa. 16201

[21] Appl. No.: 347,517

[22] Filed: May 3, 1989

Related U.S. Patent Documents

Reissue of:

[64] Patent No.: 4,662,229
Issued: May 5, 1987
Appl. No.: 769,372
Filed: Aug. 26, 1985

[51] Int. Cl.[5] ..... G01N 3/02

[52] U.S. Cl. ..... 73/859

[58] Field of Search ..... 73/856, 859, 860, 833; 279/60, 1 R, 1 ME; 269/254 R, 287

[56] References Cited

U.S. PATENT DOCUMENTS

| | | | |
|---|---|---|---|
| 1,510,896 | 10/1924 | McConnell | 279/60 |
| 2,245,316 | 6/1941 | Amsler | 73/859 |
| 2,419,711 | 4/1947 | Dillon | 73/833 |
| 2,447,660 | 8/1948 | Miklowitz | 73/859 |
| 2,537,322 | 1/1951 | Wanzenberg | 73/859 |
| 2,613,941 | 10/1952 | Gridley | 279/60 |
| 2,676,381 | 4/1954 | Holmes | 73/859 |
| 3,224,259 | 12/1965 | De Nicola | 73/859 |
| 3,403,549 | 10/1968 | Griffen | 73/859 |

*Primary Examiner*—Robert R. Raevis
*Attorney, Agent, or Firm*—Lawrence G. Zurawsky; Thomas F. Shanahan

[57] ABSTRACT

Grip apparatus for use with tensile stress testing apparatus includes a housing having connecting means on the top of the housing for connecting the grip apparatus to the tensile stress testing apparatus. A first elongated bore extends from the bottom of the housing through a portion of the housing parallel to the longitudinal axis of the housing to form a receptacle for a test piece. A pair of second elongated bores extend from the top surface of the housing, converging toward the bottom surface of the housing, with the lower end of each second bore opening into the first bore. Each of said second bores contains a slidable grip bar extending into the first bore and having a grip insert secured on the lower end of the grip bar. A spring loaded release mechanism normally retains the grip bars and grip inserts in a closed position and can be manually operated to release the inserts and grip bars by sliding the grip bars upwardly through the second bores.

22 Claims, 3 Drawing Sheets

GRIP ASSEMBLY

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to grip apparatus for use with tensile stress testing apparatus providing a relatively light weight, strong grip assembly which enables the rapid and easy removal and replacement of the grip jaw inserts, without disassembly of the grip apparatus from the testing apparatus.

2. Description of the Prior Art

In the prior art, tensile stress testing apparatus has been subject to many disadvantages, especially when such prior art testing apparatus is used for testing high tensile strength materials subject to tensile stresses in the range of several tens of thousands of pounds per square inch. The prior art devices generally are constructed of heavy materials resulting in substantial total weight. In addition, the prior art devices involve complicated structures that are expensive to manufacture. Furthermore, removal and replacement of grip jaws in prior art devices requires substantial disassembly of the grip apparatus and often requires removal of the grip apparatus from the testing device.

Canadian Pat. No. 446,096 describes grip apparatus comprising a pair of rectangular grip blocks, each of which is secured in one of the crossheads of the tensile stress testing apparatus. Each grip block has a V-shaped recess which contains one or more grip inserts. The grip insert is secured in the grip block by an aligning plate at the bottom of the block and by a removable washer at the top of the block. To provide more positive gripping action, the gripping face of each insert slopes inwardly (toward the test piece) toward its upper end and the back surface of each insert is provided with finely cut teeth or cross-cut ridges to provide a more positive contact between the V-shaped recess and the back of the grip insert. That patent does not disclose the grip housing containing the readily removable and adjustable grip bars and grip inserts of the apparatus of this invention.

Soviet Union Pat. No. 800,797 discloses a grip housing having four rectangular grooves arranged in a cross-shaped pattern. Each groove is rectangular in transverse cross-section and secures a rectangular grip insert. Each insert has a verticle face adapted to engage the test piece and a sloping slide surface which engages a sloping surface in the groove of the grip housing. Each pair of opposing grooves in the housing forms a matched pair, each being a mirror image of the other. Each sloping side wall of one pair of grip inserts forms an angle (a) with the longitudinal axis of the housing, and each sloping side wall of each of the other pair of inserts forms a different angle (b) with the longitudinal axis of the housing. The ratio of those inclination angles is equal to the ratio of the transverse strains in the two perpendicular directions and is also equal to the ratio of the Poisson coefficients in the mutually perpendiculr directions. In that device, the end of the test piece secured in the grip jaws must be rectangular in transverse cross-section and must be of sufficient size to abut the surfaces of all of the grip jaws in a substantially close tolerance fit. That patent does not disclose the apparatus of this invention comprising a housing containing a pair of grip bores each containing a grip bar and grip jaws which are easily and readily removable and replaceable without substantial disassembly of the apparatus.

U.S. Pat. No. 2,419,711 describes grip apparatus designed to withstand test loads of up to 10,000 pounds. The apparatus includes a slotted block of steel forming a base member which supports a pair of steel block jaw holders having inclined jaw engaging faces. Each of a pair of grip jaws has a slot in its back surface engaging a pin extending from the inclined surface of the jaw holder. That device is held in assembly by a clamp band and set screw, which is used to apply the initial gripping force to the test piece. That device is a relatively heavy assembly of complicated construction that requires complete disassembly of the apparatus to permit removal or replacement of the grip jaws. In addition, that patent does not disclose the apparatus of this invention comprising a light weight grip assembly capable of sustaining test forces in excess of 30,000 pounds and including a housing having grip bores containing grip bars supporting grip jaws that are easily and readily removable and replaceable without substantial disassembly of the apparatus.

U.S. Pat. No. 2,537,322 describes a grip apparatus having a relatively complicated structure comprising at least a threaded shank, a clamp head, a clamp nut, and a pair of clamp jaws, all of which must be actuated cooperatively to provide the required gripping force. The device shown in that patent weighs approximately one pound but permits tensile stress only to approximately 250 pounds when the parts are made of ordinary steel. When high tensile stresses are required, the structural elements must be made of special high tensile steel and the structural elements must be of larger size. That patent does not describe a structure capable of operating at tensile stresses in excess of 30,000 pounds per square inch, such as that described in this invention. In addition, that patent does not disclose the structure including a grip housing enclosing readily removable grip bars on which are mounted grip jaws that are easily and readily removable and replaceable from the apparatus without substantial disassembly of the apparatus.

U.S. Pat. No. 3,403,549 discloses grip apparatus comprising a housing having a hollow interior which provides a receptable to enclose a pair of grip jaws. Each of the grip jaws has a seat in its top surface adapted to receive a helical spring, mounted in the housing receptacle, to maintain the jaws in closed condition. Each of the jaws also has an inclined groove adapted to receive a lever arm of a cam mechanism that is mutually operated by a lever to release the grip jaws. The assembly comprising the grip jaws, springs, and cam is covered by a face plate which is secured by threaded fasteners onto the housing side walls. The inclined top surface of the housing must be perpendicular to the inclined wedging surface of the interior walls of the housing. Similarly, the top surface of each grip jaw is inclined and must be perpendicular to the inclined interior wall surface of the housing. That patent indicates further that removal of material from the housing weakens the housing and reduces the maximum stress to which the grip apparatus may be subjected; therefore, that patent indicates that, when slots are to be provided, the size of the housing must be increased to compensate for the loss of strength attributed to the slots. The device disclosed in that patent requires substantial disassembly of the grip apparatus to enable removal and replacement of the grip jaws. In addition, that patent does not disclose the apparatus of this invention comprising a relatively light weight housing having grip bores containing grip bars carrying grip jaw inserts that are readily removable and replaceable without substantial disassembly of the housing.

There remains a need for a grip apparatus for use with tensile stress testing devices providing a strong, relatively light weight grip apparatus that can be readily adapted for use with existing tensile stress testing devices to test high tensile strength materials without risk of failure of the grip apparatus. There remains a further need for such grip apparatus which permits easy and rapid removal and replacement of the grip jaws without removal of the grip apparatus from the test device and without substantial disassembly of the grip apparatus.

SUMMARY OF THE INVENTION

In accordance with the present invention there is provided a grip apparatus that includes a housing, connecting means for connecting the housing to a tensile stress testing apparatus, a first bore extending from the bottom of the housing upwardly through a portion of the housing, a pair of second bores extending from the top of the housing through the housing and converging toward the bottom of the housing with the lower end of each second bore opening into the first bore, a pair of grip bars each slideably mounted in one of the second bores, and grip insert means secured near the end of each grip bar within the first bore.

In a preferred embodiment of the apparatus of this invention each of the second bores is circular in cross-section and each of the grip bars is cylindrical.

In a further preferred embodiment of the apparatus of this invention, the angle formed between the central longitudinal axis of each second bore and the central longitudinal axis through the first bore is within the range of from 10 degrees to 40 degrees.

In another preferred embodiment of the apparatus of this invention, the angle formed between the central longitudinal axis through each of the second bores and the central longitudinal axis through the first bore is 15 degrees.

Accordingly, it is an object of the present invention to provide grip apparatus which is of relatively simple and relatively inexpensive construction and which is relatively light weight while providing means for testing high tensile strength materials at stresses in the range of several tens of thousands of pounds per square inch.

It is another object of the present invention to provide grip apparatus that is readily adapted for use with existing testing devices for the testing of materials over a wide range of tensile strengths.

Another object of the present invention is to provide grip apparatus which enables the easy and rapid removal and replacement of the grip jaws without substantial disassembly of the grip assembly and without removing the grip apparatus from the testing device.

Those and other objects of the present invention will be more completely disclosed and described in the following specification, the accompanying drawings and the appended claims.

DESCRIPTION OF THE PREFERRED EMBODIMENT

Figure 1:
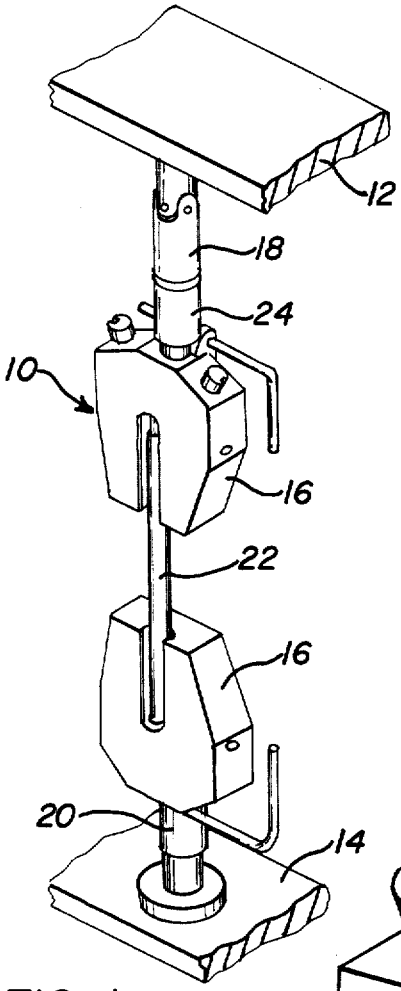
FIG. 1 is a diagramatic representation of a tensile stress testing apparatus incorporating the grip apparatus of the present invention.

Referring to the drawings, and particularly to FIG. 1, a tensile stress testing apparatus is shown diagrammatically and is indicated generally by reference numeral 10. Testing apparatus 10 consistsof a top member 12 and a base 14. A grip apparatus 16 of the present invention is attached by suitable means 18 to the top member 12 of testing apparatus 10 and an identical grip apparatus 16 is attached by suitable means 20 to the base 14 of testing apparatus 10. A test piece 22 is secured at either end in one of the grip apparatus 16 for testing. Stress means 24, shown diagrammatically in FIG. 1, can be any of the conventional means employed with testing apparatus 10 to apply tensile stress to test piece 22 and to record the amount of tensile stress so applied.

Figure 2:
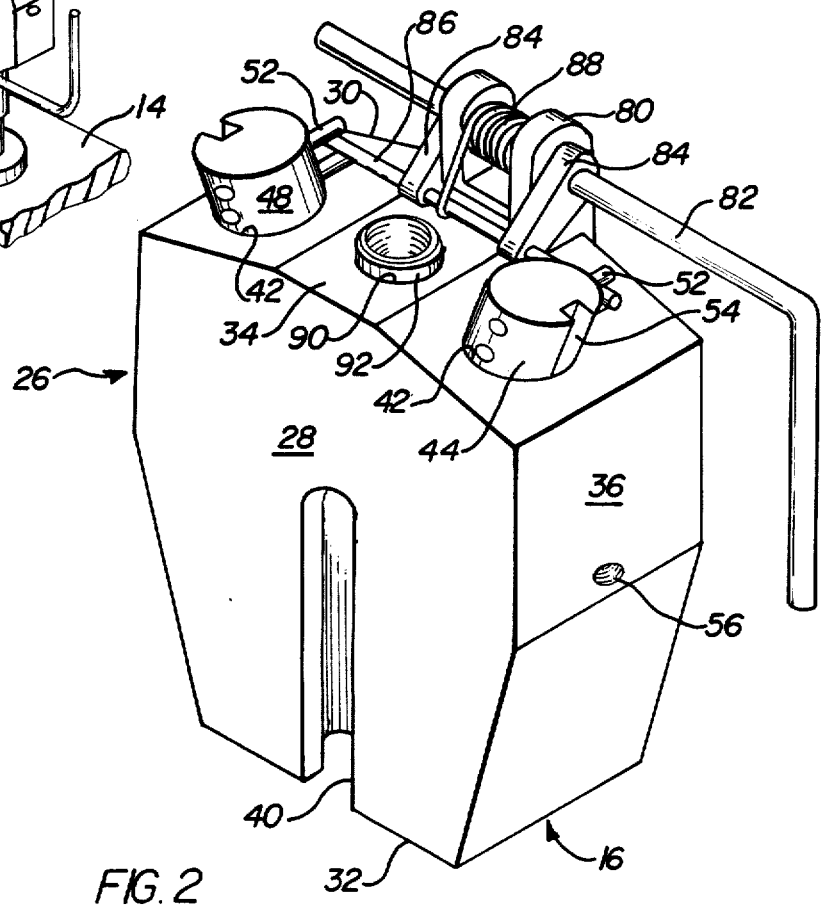
FIG. 2 is an isometric view of the grip apparatus of the present invention.

In FIG. 2, the grip apparatus is indicated generally by reference numeral 16 and comprises a housing 26 having a front surface 28, a rear surface 30, a bottom surface 32, a top surface 34, and opposing side surfaces 36. In a preferred embodiment of this invention, housing 26 is of unitary construction consisting of a single, integral piece of material. Housing 26 can be constructed of any suitable material providing the strength and rigidity required for the particular range of tensile stress to be applied to a selected work piece. For example, for high stress use, housing 26 can be constructed of steel, or other suitable metal. For low stress use for testing materials having low tensile strength such as thin gauge wire or plastic materials, housing 26 can be constructed of plastic or other strong, rigid, non-metallic materials. In a preferred embodiment of this invention, for use with high tensile strength materials having a tensile strength in excess of 30 thousand pounds per square inch, housing 26 has been constructed of aluminum.

Figure 4:
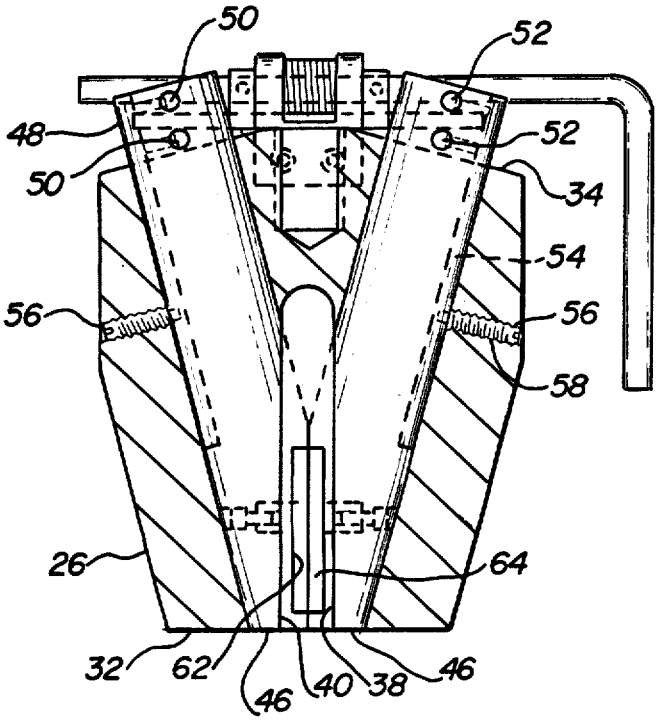
FIG. 4 is a side elevation view, partially in cross-section, of the grip apparatus of the present invention.

Referring to FIGS. 2 and 4, a first bore 38 extends from the bottom surface 32 of housing 26 upwardly through a portion of housing 26 parallel to the longitudinal axis of housing 26. In some embodiments of the apparatus of this invention, the central longitudinal axis of first bore 38 may coincide with the central longitudinal axis of housing 26; however, in a preferred embodiment of this invention, the central longitudinal axis of first bore 38 is parallel to, but displaced from, the central longitudinal axis of housing 26, with the circumference of first bore 38 being equally spaced between the side edges of bottom surface 32 of housing 26 and with the circumference of first bore 38 on the bottom surface 32 of housing 26 being positioned substantially closer to front surface 28 of housing 26 than it is to rear surface 30 of housing 26. Such "off-center" orientation of first bore 38 in housing 26 enables easier acces to an operator while removing or inserting a test piece 22. In a preferred embodiment of this invention, first bore 38 has a circular transverse cross-section; however, in other embodiments of this invention, first bore 38 may have a polygonal transverse cross-section or a non-round, curved transverse cross-section.

As shown in FIGS. 2 and 4, a slot 40 is formed in a portion of the front surface 28 of housing 26 in alignment with first bore 38 and opening into first bore 38 to enable the placement and removal of test piece 22 in and from housing 26. Although slot 40 provides operational convenience in use, slot 40 is not an essential element of structure in the apparatus of this invention. In certain preferred embodiments of this invention, slot 40 can be omitted to provide even greater strength of the apparatus.

Figure 3:
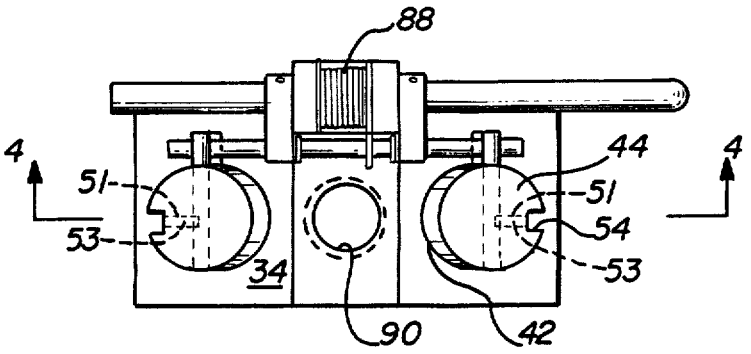
FIG. 3 is a top plan view of the grip apparatus of the present invention.

As shown in FIGS. 2, 3 and 4, a pair of second bores 42 extend from the top surface 34 of housing 26 through housing 26 to the bottom surface 32. Second bores 42 mutually converge and open into first bore 38 as second bores 42 extend toward bottom surface 32 of housing 26. In a preferred embodiment of this invention, second bores 42 are circular in transverse cross-section; however, in other embodiments of this invention, second bores 42 may be either polygonal or of curved, non-round transverse cross-section.

In each of the second bores 42, there is slidably mounted a grip bar 44, with extends downwardly through housing 26 and has a bottom surface 46, which may be flush with bottom surface 32 of housing 26. In a preferred embodiment of this invention, bottom surface 46 of grip bar 44 is spaced vertically from bottom surface 32 of housing 26 within first bore 38.

An upper portion 48 of grip bar 44 extends beyond top surface 34 of housing 26. A pair of mutually spaced, aligned holes 50 extend through upper portion 48 of grip bar 44. Each hole 50 contains a pin 52, extending outwardly from grip bar 44 toward rear surface of housing 26. The function of pins 52 is described more fully below.

The peripheral transverse configuration of grip bar 44 conforms to the shape of the transverse cross-section of second bore 42 in a manner adapted to provide a close tolerance, readily slidable fit between the surfaces of second bore 42 and grip bar 44 while preventing damage to those surfaces while the grip apparatus is in use. In a preferred embodiment of this invention, grip bar 44 is cylindrical and conforms to a circular transverse cross-section of second bore 42. In other embodiments of this invention, the transverse cross-section of grip bar 44 can be polygonal or of a non-round, curved configuration. In all instances, the cross-sectional configuration of grip bar 44 conforms to the cross-section configuration of second bore 42.

A groove 54 is formed in the side of grip bar 44 and extends a portion of the length of grip bar 44 adjacent the side surface 36 of housing 26. In the upper end of each groove 54 adjacent each hole 50 and each pin 52, a threaded bore 51 extends from groove 54 into hole 50 and secures a threaded set screw 53 which abuts pin 52 and secures pin 52 in place.

In assembly, groove 54 is aligned with an adjacent hole 56 extending from side surface 36 of housing 26 into the second bore 42. Each hole 56 is threaded and contains a threaded pin 58 which extends into groove 54 to enable proper slidable alignment of grip bar 44 and to prevent turning of grip bar 44 when the grip apparatus 16 is in use. Alternatively, threaded holes 56 and threaded pins 58 may be omitted when grip bars 44 and second bores 42 have a polygonal transverse cross-section, or other configuration, that prevents turning of grip bars 44 in use.

In use, pins 58 can be adjusted in their respective grooves 54 to secure one of grip bars 44 tightly in position without substantial movement while the other grip bar 44 is permitted to "float" or moved relatively freely within a preselected degree of tolerance to provide a firm grip on the work piece, especially when the work piece has an irregular shape or irregular surface.

Figure 5:
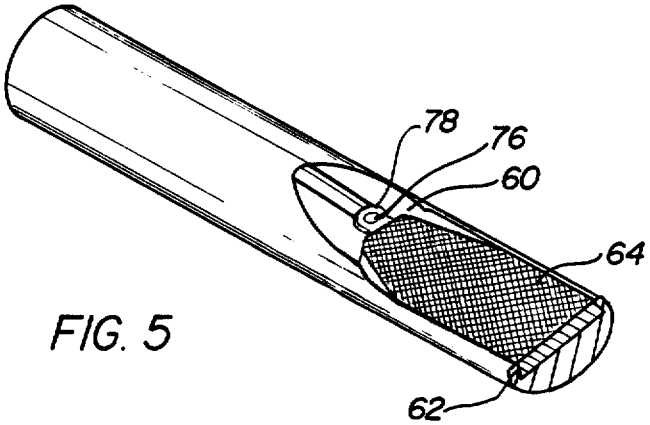
FIG. 5 is an isometric view, partially in cross-section, of a grip bar used with the grip apparatus of the present invention, with a single grip jaw insert mounted on the grip bar.
Figure 6:
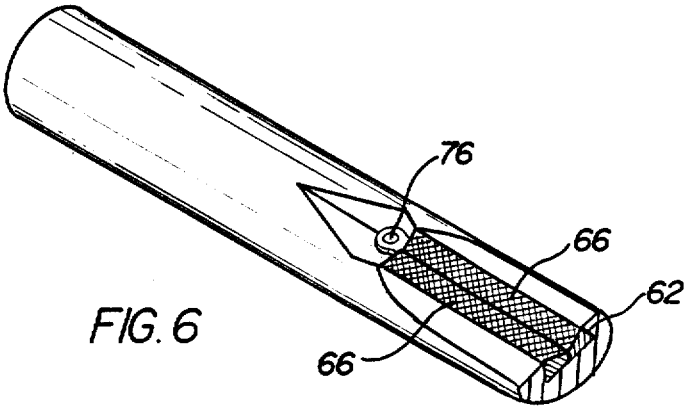
FIG. 6 is an isometric view, partially in cross-section, of a grip bar used with the apparatus of the present invention, with a plurality of grip jaw inserts mounted on the grip bar.

As shown in FIGS. 4, 5 and 6 each of the grip bars 44 has a planar surface 60 formed in the lower portion of grip bar 44. A receptable 62 is formed in the planar surface 60 of grip bar 44 to receive and secure a grip jaw insert 64 and 66 in grip bar 44.

FIG. 5 shows an embodiment of this invention in which a single grip jaw insert 64, having a cross-scored face, is mounted on grip bar 44. FIG. 6 shown an embodiment of this invention in which a plurality of grip jaw inserts 66 are secured, in mutual angular relationship, on grip bar 44. The selection and use of a single grip jaw insert as shown in FIG. 5, or of a plurality of grip jaw inserts as shown in FIG. 6, is determined by the peripheral configuration of the test piece 22 to be secured by the grip jaw inserts in a particular application of the apparatus of this invention.

Figure 7:
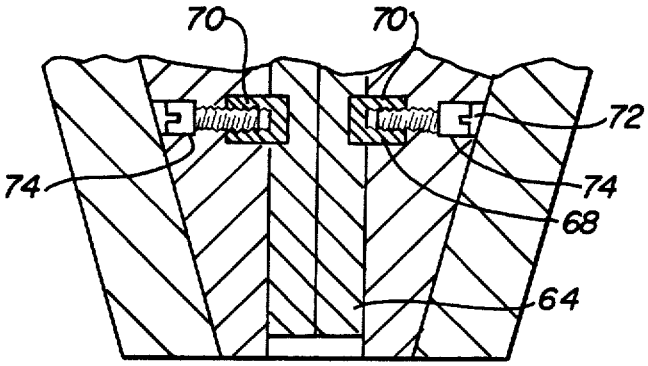
FIG. 7 is a fragmented view, partially in cross-section, showing the means of connecting the grip jaw inserts to the grip bars.
Figure 8:
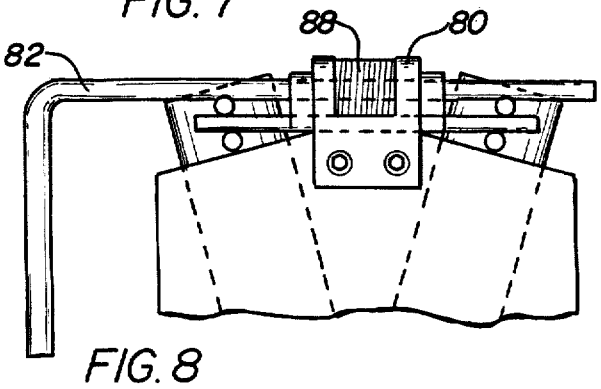
FIG. 8 is a fragmented, rear elevation view of the grip bar release means attached to the top of the housing.

The grip jaw insert 64 or 66 is mounted on grip bar 44 as shown in FIG. 7. An internally threaded collar 68 extends from the rear surface of grip jaw insert 64 or 66 into a seat 70 formed in the planar surface of grip bar 44. A counter sunk hole 72 extends from the rear surface of grip bar 44 in alignment with the threaded collar 68 on grip jaw insert 64 or 66 and a threaded locking screw 74 extends through hole 72 into collar 68 to secure grip jaw insert 64 or 66 on grip bar 44. An additional, or alternative, means for securing the grip jaw insert to the grip bar is shown in FIG. 5 wherein a threaded lock nut 76 is shown secured on the planar surface 60 of grip bar 44 through a tab 78 extending from grip jaw insert 64. Alternatively, the grip jaw inserts can be further secured to the grip bar by means of spring clips or other suitable attachment means, not shown in the drawings.

Grip bars 44 and grip jaw inserts 64 and 66 of the apparatus of this invention can be made of any suitable rigid material having sufficient strength to withstand the range of tensile stress to be applied to a particular work piece. In a preferred embodiment of this invention, grip bars 44 and grip jaw inserts 64 and 66 are made of steel.

As shown in FIGS. 2, 3, 4 and 8, means for manual adjustment, release, and removal of grip bars 44 from the second bores 42 include a yoke 80 mounted on the rear and top surfaces of housing 26. A handle 82 is rotatably mounted in yoke 80. A pair of levers 84 are fixedly secured at one end to handle 82. A bar 86 extends through the ends of the levers 84 remote from handle 82. Bar 86 is loosely engaged between the pins 52 on grip bars 44. A spring 88 is mounted on handle 82 within yoke 80 and is attached to bar 86 to exert sufficient force in a downward direction to maintain grip bars 44 in a normally closed condition. Handle 82 may be rotated manually against the force exerted by spring 88 to raise grip bars 44 on open grip jaw inserts 64 to permit insertion of a test piece 22 between the jaws of the apparatus. When the testing apparatus 10 is actuated to move the grip assemblies 16 away from each other, the forces exerted among the test piece, the grip jaw inserts and the grip bars provide additional gripping force among the grip bars, the grip jaws and the test piece.

A threaded hole 90 in the top surface 34 of housing 26 is adapted to receive a connector 92 having both external and internal threads. Hole 90 and connector 92, or other suitable connecting means, can be adapted to enable connection of grip apparatus 16 to any type of existing tensile stress testing apparatus 10.

Maintenance of a suitable angle formed between grip bars 44 is useful in providing a grip apparatus of exceptional strength and gripping force, even when the housing is constructed of light weight materials such as aluminum. One convenient manner of describing that angle is the angle formed between the central longitudinal axis of the second bore and the central longitudinal axis through the first bore 38. A suitable range for that angle in the apparatus of this invention is from approximately 10 degrees to approximately 40 degrees. In a preferred embodiment of this invention, that angle is 15 degrees.

Tensile stress tests were performed using a lower grip apparatus consisting of a prior art device constructed of steel and weighing approximately 55 pounds. The upper grip apparatus employed was the apparatus of this invention consisting of an aluminum housing with cylindrical steel grip bars, with said grip apparatus having a total weight of approximately 25 pounds. The angle between the central longitudinal axis of the second bore and the central longitudinal axis through the first bore was 15 degrees. Various tensile strength tests were performed on a plurality of steel test pieces, with the result that, at a tensile stress of 36,000 pounds per square inch, the prior art lower grip apparatus began to fail and slip, while the upper grip apparatus of this invention continued to function satisfactorily, without mishap.

The apparatus of the invention provides grip apparatus that can be used with new or previously known tensile stress testing apparatus to test low, medium or high tensile strength materials without risk of failure of the grip apparatus. The grip apparatus of this invention is of relatively simple and inexpensive construction, can be made of relatively light weight materials, and can be so constructed as to have a relatively low gross weight for the grip apparatus. The apparatus of this invention provides the further advantage of permitting easy and rapid removal and replacement of the grip jaws without removal of the grip apparatus from the test device and without substantial disassembly of the grip apparatus.

Although the apparatus of this invention has been described with respect to its use with tensile stress testing apparatus, the apparatus of this invention can be used with other types of material strength or stress testing apparatus, such as testing apparatus used to test resistance to torsion or bending.

According to the provisions of the patent statutes, I have explained the principle, preferred construction and mode of operation of my invention and have illustrated and described what I now consider to represent its best embodiments. However, it should be understood that, within the scope of the appended claims the invention may be practiced otherwise than as specifically illustrated and described.

Therefore, claim:

1. Grip apparatus for use with tensile stress testing apparatus adapted to measure tensile stress in a test specimen comprising a housing having a bottom surface, a top surface, opposing front and rear surfaces and opposing side surfaces, connecting means secured to the top surface of said housing for connecting said grip apparatus to said tensile stress testing apparatus, a first bore extending from said bottom surface upwardly through a portion of said housing, a pair of second bores extending from said top surface of said housing through said housing and converging toward the bottom surface of said housing, with the lower end of each of said second bores opening into said first bore, a pair of grip bars, one of said grip bars being slidably mounted in one of said second [,] and the other of said grip bars being slidably mounted in the other of said second bores, *said grip bars being enclosed by said second bores and conforming in cross-section to the cross-section of said second bores,* each of said grip bars extending above the said top surface and each of said grip bars having grip insert means secured on the lower end of said grip bar at least partially within said first bore, the said grip insert means being opposed and being adapted to compressively engage opposed surfaces of [a] said test specimen, whereby application of tensile stress to said test specimen increases the compressive engagement of said grip insert means with said test specimen.

2. The grip apparatus of claim 1 wherein each of said second bores is circular in cross-section, and wherein each of said grip bars is cylindrical.

3. The grip apparatus of claim 2 wherein each of said grip bars has a groove extending longitudinally along a portion of its surface adjacent said side surface of said housing, and means within said housing engaged with at least one said groove to prevent turning of the grip bar having the engaged groove.

4. The grip apparatus of claim 1 including means for introducing one end of a said test specimen into said grip apparatus, said means comprising a slot extending through said front surface of said housing and opening into said first bore.

5. The grip apparatus of claim 1 wherein said housing is constructed of alluminum.

6. The grip apparatus of claim 1 wherein each of said grip bars has formed [in ] *on* its lower end a receptacle containing *said grip insert means and said grip insert means comprises* a plurality of grip insert members.

7. The grip apparatus of claim 1 including release means mounted on said housing and constructed and arranged to engage each of said grip bars for selective release of said grip bars by movement of said grip bars longitudinally upwardly within the respective ones of said second bores.

8. The grip apparatus of claim 7 wherein the said release means comprises:

first release elements mounted on the upper end of each said grip for above the said top surface, and second release elements mounted on said housing and constructed and arranged to engage said first release elements for selective release of said grip bars by movement of said grip bars upwardly above the said top surface.

9. The grip apparatus of claim 1 wherein the angle formed between the central longitudinal axis of each of said second bores and the central longitudinal axis through said first bore is within the range of from 10 degrees to 40 degrees.

10. The grip apparatus of claim 9 wherein the said angle is 15 degrees.

11. In combination with a tensile stress testing apparatus comprising support means, first grip means mounted on said support means, second grip means mounted on said support means opposite and aligned with said first grip means, and actuator means mounted on said support means and connected to at least one of said first and second grip means and constructed and arranged to move at least one of said first grip means and said second grip means away from the other of said first grip means and said second grip means, the improvement wherein at least one of said first grip means and second grip means comprises the grip apparatus of claim 1.

*12. Grip apparatus for use with tensile stress testing apparatus adapted to measure tensile stress in a test specimen comprising*

*a housing having a connecting end adapted for securing said housing to said tensile stress testing apparatus,*

*a test specimen receiving end opposite said connecting end of said housing,*

*a pair of passages extending through said connecting end of said housing and converging toward said receiving end of said housing,*

*a cavity adapted for receiving one end of a test specimen within said housing, said cavity being in operative communication with said pair of passages, and*

*a pair of grip bars, one of said grip bars being slidably mounted in one of said passages and the other of said grip bars being slidably mounted in the other of said passages, said grip bars being enclosed by said passages and conforming in cross-section to the cross-section of said passages, each of said grip bars extending above said connecting end of said housing and each of said grip bars having grip means carried on its lower end, said grip means being opposed and being adapted to compressively engage opposed surfaces of a test specimen, whereby application of tensile stress to said test specimen increases the compressive engagement of said grip means with said test specimen.*

*13. The grip apparatus of claim 12 wherein each of said passages is circular in cross-section, and wherein each of said grip bars is circular.*

*14. The grip apparatus of claim 13 wherein each of said grip bars has a groove extending longitudinally along a portion of its surface adjacent a side surface of said housing, and*

*means within said housing engaged with at least one said groove to prevent turning of the grip bar having the engaged groove.*

*15. The grip apparatus of claim 12 including means for introducing one end of said test specimen into said grip apparatus through its front surface, said means comprising a slot extending through the front surface of said housing and opening into said cavity.*

*16. The grip apparatus of claim 12 wherein said housing is constructed of aluminum.*

*17. The grip apparatus of claim 12 wherein each of said grip bars has formed at its lower end a receptacle containing said grip means and said grip means comprises a plurality of grip insert members.*

*18. The grip apparatus of claim 12 including release means mounted on said housing and constructed and arranged to engage each of said grip bars for selective release of said grip bars by movement of said grip bars longitudinally upwardly within the respective ones of said passages.*

*19. The grip apparatus of claim 18 wherein said release means comprises*

*first release elements mounted on the upper end of each said grip bar above said connecting end of said housing, and*

*second release elements mounted on said housing and constructed and arranged to engage said first release elements for selective release of said grip bars by movement of said grip bars upwardly above said connecting and of said housing.*

*20. The grip apparatus of claim 12 wherein the angle formed between the central longitudinal axis of each of said passages and the central longitudinal axis through said cavity is within the range of from 10 degrees to 40 degrees.*

*21. The grip apparatus of claim 20 wherein the said angle is 15 degrees.*

*22. In combination with a tensile stress testing apparatus comprising*

*support means,*

*first grip means mounted on said support means,*

*second grip means mounted on said support means opposite and aligned with said first grip means, and*

*actuator means mounted on said support means and connected to at least one of said first and second grip means and constructed and arranged to move at least one of said first grip means and said second grip means away from the other of said first grip means and said second grip means,*

*the improvement wherein at least one of said first grip means and second grip means comprises the grip apparatus of claim 12.*

* * * * *